United States Patent [19]
Chen

[11] Patent Number: 5,239,989
[45] Date of Patent: Aug. 31, 1993

[54] SAFETY DEVICE

[76] Inventor: Chin S. Chen, 3126 Lexington Dr., Ann Arbor, Mich. 48105

[21] Appl. No.: 824,757

[22] Filed: Jan. 17, 1992

Related U.S. Application Data

[63] Continuation of Ser. No. 537,478, Jun. 13, 1990, abandoned.

[51] Int. Cl.$^5$ ............................................. A61M 15/00
[52] U.S. Cl. ........................ 128/200.24; 128/204.18; 128/206.27
[58] Field of Search ............... 206/803; 128/200.24, 128/202.11, 204.18, 205.25, 206.27

[56] References Cited

U.S. PATENT DOCUMENTS

| | | | |
|---|---|---|---|
| 2,122,897 | 7/1938 | Straw | 128/204.18 |
| 2,831,607 | 4/1958 | Berndt | 128/205.25 |
| 3,043,302 | 7/1962 | Spears et al. | 128/205.24 |
| 3,073,301 | 1/1963 | Hay et al. | 128/206.27 |
| 3,338,238 | 8/1967 | Warncke | 128/142.2 |
| 3,580,250 | 5/1971 | Oroza | 128/202.26 |
| 3,733,008 | 5/1973 | Churchill et al. | 128/202.26 |
| 3,820,538 | 6/1974 | Nakanishi | 128/142.2 |
| 3,892,234 | 7/1975 | Jones | 128/142 |
| 4,165,738 | 8/1979 | Graves et al. | 128/142.4 |
| 4,197,841 | 4/1980 | Brauer et al. | 128/202.13 |
| 4,243,155 | 1/1981 | Stewart | 128/205.24 |
| 4,265,236 | 5/1981 | Pacella | 128/203.23 |
| 4,271,834 | 6/1981 | Tanaka | 128/205.27 |
| 4,353,292 | 10/1982 | Almasi et al. | 98/50 |
| 4,460,089 | 1/1984 | Abbott | 206/527 |
| 4,473,072 | 9/1984 | Walther | 128/201.25 |
| 4,537,189 | 8/1985 | Vicenzi | 128/202.13 |
| 4,669,462 | 6/1987 | Marshall | 128/205.25 |
| 4,724,833 | 2/1988 | Bartos | 128/205.24 |
| 4,788,973 | 12/1988 | Kirchgeorg et al. | 128/205.24 |
| 4,798,203 | 1/1989 | Bartos | 128/205.22 |
| 4,905,684 | 3/1990 | Heffer | 128/202.13 |

FOREIGN PATENT DOCUMENTS 929172  6/1955  Fed. Rep. of Germany.

OTHER PUBLICATIONS

British Medical Journal, Dec. 27, 1969 vol. 4, p. 786 "Actifed in Space".

Primary Examiner—Edgar S. Burr
Assistant Examiner—Aaron J. Lewis
Attorney, Agent, or Firm—Krass & Young

[57] ABSTRACT

A portable emergency breathing apparatus provides both a source of breathing gas and a source of light to a person confronted by an emergency situation. Breathing gas from a supply container is distributed through a mouthpiece to the user. Further, a flashlight is removably affixed to the breathing gas supply container for use by the user. The apparatus is stored within a storage container adapted for convenient storage and transition to use of the emergency apparatus. The storage container comprises a storage body and cap member. The mouthpiece of the breathing apparatus is secured proximate the interior surface of the capping member. In this manner, access to the capping member provides for immediate access to the mouthpiece and facilitates removal of the emergency equipment from the storage container.

19 Claims, 2 Drawing Sheets

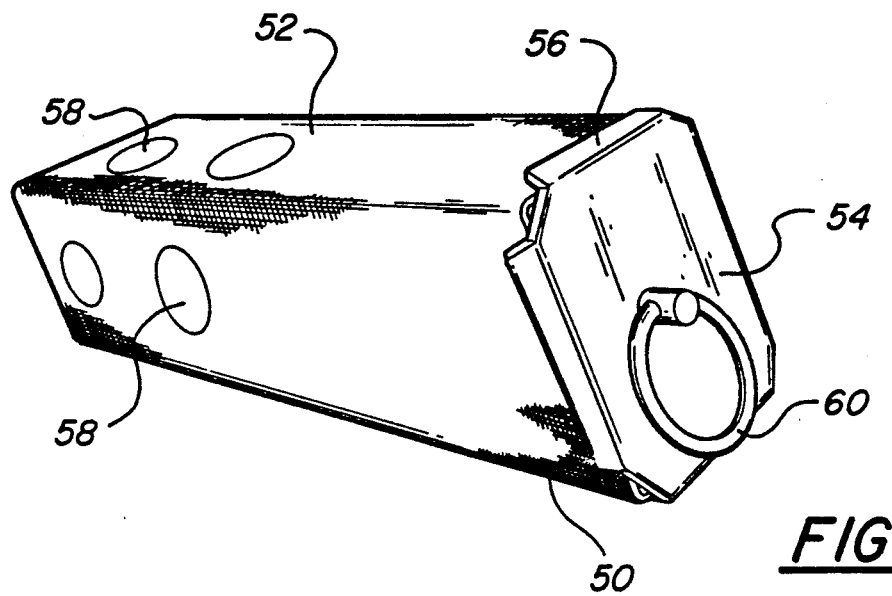
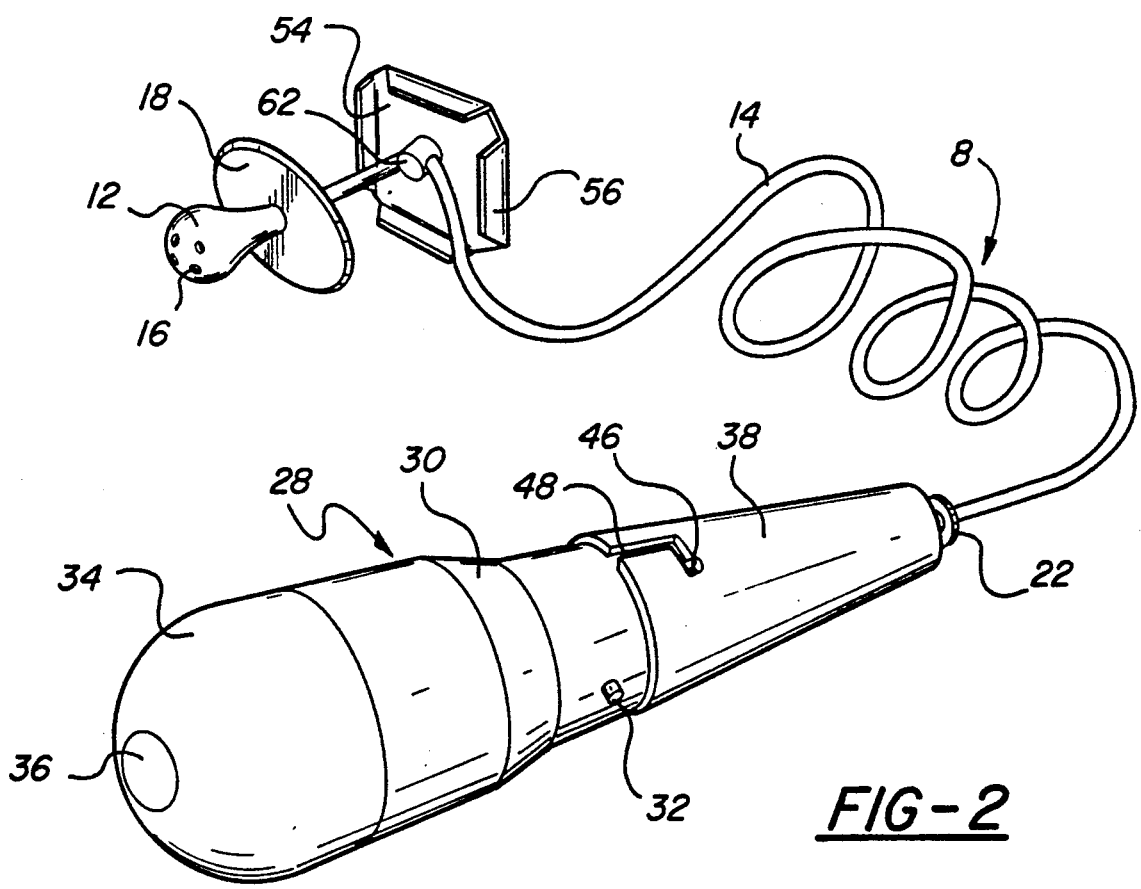

SAFETY DEVICE

This is a continuation of copending application Ser. No. 07/537,478 filed on Jun. 13, 1990, now abandoned.

FIELD OF THE INVENTION

The present invention relates generally to safety apparatus for providing a portable supply of emergency breathing gas.

BACKGROUND OF THE INVENTION

There are numerous potential emergency situations requiring safety devices which provide a portable supply of breathing gas. These situations typically include the presence of matter, such as smoke or water, which obstructs normal breathing. Such situations include vehicles accidentally submerged underwater, vehicle fires, building fire, chemical fires, vapor leaks, and the like.

In these emergency situations, occupants of the vehicles or buildings require a source of breathing gas. The source of breathing gas must meet certain criteria. It must be sufficiently small so as not to obstruct the occupant's normal use of the vehicle or area of the building. Further, the source of the breathing gas must be sufficiently portable to provide the occupant with a source of breathing gas while he effectuates an escape from the emergency surroundings. Typically a five or ten minute breathing gas supply has been provided for such emergencies. This relatively small amount of gas can be supplied in a compact apparatus.

However, another aspect of these emergency situations is frequently overlooked by the prior art. When an occupant of a vehicle or a building is inundated with water or smoke, his surroundings are substantially hidden from view. When vehicles, such as trains, airplanes, and automobiles, are submerged in water, their interior portions typically become blanketed in darkness. Further, smoke filled rooms or vehicles have similarly reduced visibility. The occupant needs to have both a supply of breathing gas and a source of light available to effectuate an escape in the relatively short amount of time typically available.

Consequently, a need exists for a safety device which provides both a source of breathing gas and a source of light.

SUMMARY OF THE INVENTION

The present invention provides for a portable emergency breathing apparatus having a breathing gas supply container which supplies breathing gas to a mouthpiece. A valve disposed between the mouthpiece and the breathing gas supply container controls the flow of gas to the mouthpiece. A flashlight removably affixed to the breathing gas supply container provides the supply of light necessary for the emergency situation. Once a person faced with an emergency situation locates the present invention he has located both the supply of breathing gas and the source of light.

The invention also provides for a storage container for receiving the portable emergency breathing apparatus therein. The storage container includes a container body and cap member. The container body is configured with openings to allow use of the flashlight while the flashlight is received within the storage container.

The cap member of the storage container includes a ring handle secured to the exterior surface thereof. The handle is preferably luminescent so as to be visible under any light conditions. To effectuate the transition from storage to use, the mouthpiece of the breathing apparatus is preferably secured proximate the interior surface of the cap member. This causes the entire apparatus to be withdrawn from the storage container upon removal of the cap member from the container body. Most importantly, it effectively places the mouthpiece in the hands of the occupant upon removal of the cap member.

The flashlight preferably is waterproof and configured to float vertically in the water. A number of configurations of the flashlight are anticipated to provide both a source of light for occupant use and a signalling device for rescuer's use. Various patterns of colored light or blinking lights can be utilized.

BRIEF DESCRIPTION OF THE DRAWINGS

These and other objects and aspects of the present invention will become clear from the following description of the invention, in which:

FIG. 1 illustrates a perspective view of the storage container in its closed configuration;

FIG. 2 illustrates a perspective view of the apparatus removed from the storage container.

DESCRIPTION OF THE PREFERRED EMBODIMENT

Figure 3:
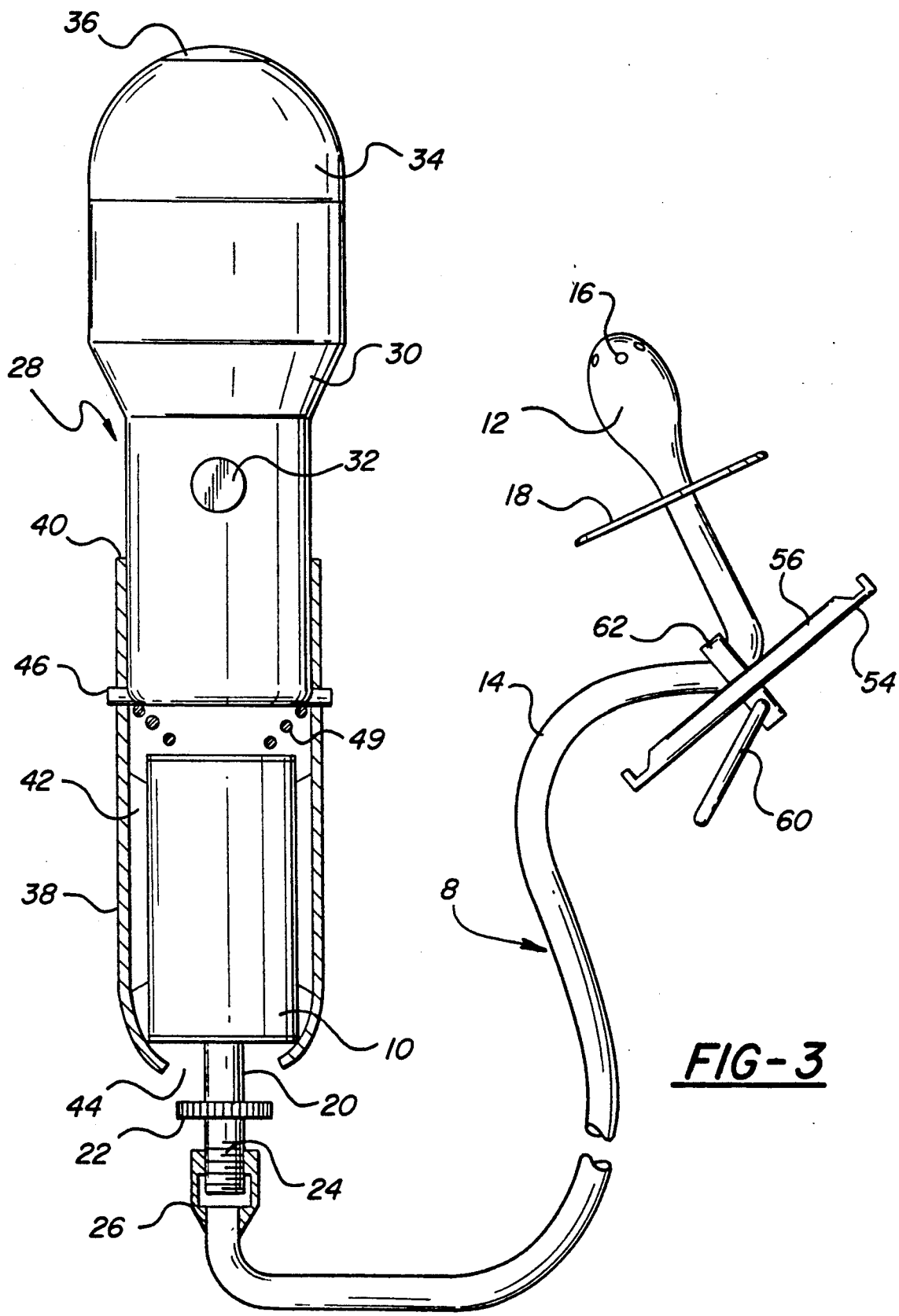
FIG. 3 illustrates a cutaway view of the apparatus removed from the storage container.

The present invention relates to a safety device which provides both a source of breathing gas and a source of light for a person confronted with an emergency situation. FIGS. 1 through 3 illustrate the portable emergency breathing apparatus in greater detail. FIGS. 1 through 3 will be referred to collectively for the purpose of illustrating the preferred embodiment of the invention hereinafter.

The present invention provides breathing gas apparatus 8 for use in an emergency which obstructs normal breathing. A breathing gas supply container 10 communicates with mouthpiece 12 to provide a supply of breathing gas to the user. The breathing gas supply container 10 communicates with the mouthpiece 12 through a length of elastomeric tubing 14. Tubing 14 is preferably composed of a elastomeric material, such as rubber or a synthetic polymer, enabling it to flex during storage and use without cracking, breaking or otherwise failing. Openings 16 in the mouthpiece 12 transmit the breathing gas to the user. The stop plate 18 prevents the mouthpiece 12 from being improperly inserted into the user's mouth.

A valve 20 controls the flow of gas from the breathing gas supply container 10 to the mouthpiece 12. Valve knob 22, disposed proximate the container 10, allows for manual control of the valve 20. In the preferred embodiment, valve 20 is attached at one end to breathing gas supply container 10, and at the other end to the elastomeric tubing 14. The connection to these components can be accomplished through typical connection methods, such as threaded section 24 and adaptor 26 which cooperate to secure the valve 20 to the elastomeric tubing 14 as shown. This is but one example of placement of the valve 20 to control the flow of gas from the gas supply container 10 to the mouthpiece 12. The valve 20 could also be conveniently disposed proximate the mouthpiece 12 (i.e. between the tubing 14 and the mouthpiece 12). The invention anticipates conveniently locating the valve knob 22 for operating the valve 20 to control the flow of breathing gas during the emergency.

The flashlight 28 utilizes a waterproof flashlight housing 30 and a on-off actuator switch 32. The flashlight 28 is configured to include a variety of possible lens mechanisms. Typically, there are two uses for the flashlight 28. First, the flashlight 28 serves to provide light for the operator to use in effectuating escape from his surroundings. Secondly, the flashlight 28 serves to signal others of the existence of the user in the emergency situation. Given this two-fold use for the flashlight 28, a number of possible flashlight configurations can be anticipated. Preferably, the flashlight would include a red signal portion 34 and a clear spotlight portion 36. In this manner, an operator can direct a beam of light to illuminate portions of his surroundings using the spotlight 36. At the same time, the red signal portion 34 constantly emits a signal for potential rescuers. Numerous other embodiments can be anticipated without departing from the scope of the invention. These would include the use of a variety of colors, blink patterns, or arrays of bulb and lens assemblies providing these distinct functions.

The flashlight 28 and breathing apparatus 8 assemblies are removably interconnected by a connector housing 38. The breathing gas supply container 10 is inserted through an internal access opening 40 and located within the connector housing 38. The container 10 is frictionally engaged by support members 42 and positioned to allow the valve 20 to engage container 10 through a separate opening 44 in the bottom of connector housing 38. The internal access opening 40 is effectively sealed by insertion of a portion of the flashlight 28 therein. Flashlight 28 has a pair of engagement studs 46 which communicate with attachment slots 48 in connector housing 38. Thus, flashlight 28 can be inserted into housing 38 and rotated to removably secure the flashlight 28 thereto. Spring 49, shown in cutaway view in FIG. 3, aids in positioning the container 10 within housing 38 by preventing container 10 from sliding therein.

Preferably, the connector housing 38 is made of metal. This provides a strong housing 38 which protects the container 10 from puncture. Also, in the event of the rupture of the container 10 it contains any potential flying debris.

It is anticipated that the safety device of the present invention will be kept in a storage container 50 to prevent damage to its associated elements. Storage container 50 includes container body 52 and cap member 54. The cap member 54 includes lip flanges 56 which engage container body 52 to secure the apparatus within the storage container 50. The storage container 50 can also be made from metal to protect the overall apparatus.

The container body 52 includes openings 58 which provide access to the flashlight 28 while the entire apparatus is stored therein. More specifically, the openings 58 allow for use of the flashlight while the apparatus is within the storage container 50. Such use is anticipated when the user is not confronted by an emergency situation, but rather needs a source of light for a short time or wants to test the flashlight at routine intervals. Typically, the spotlight 36 portion of the flashlight 28 is stored proximate the rear end of storage body 52. An opening 58 in the end of container body 52 (not shown in the drawings) allows light to be emitted from within the storage container 50. Openings 58 in the sides of container body 52 provide for access to the on-off switch 32 and allow the signal light to be emitted from within the storage container 50.

Cap member 54 is designed to facilitate the use of the present invention in emergency situations. Ring 60 provides an efficient handle for removal of the cap member 54 from the container body 52. Ring 60 is preferably luminescent so as to be visible under any light conditions. This provides an easy target for a person confronted with an emergency situation.

The design of cap member 54 also facilitates the removal of the apparatus from within the container 50. The mouthpiece 12 is secured proximate the interior surface of the cap member 54 by retainer 62. By being so secured, the mouthpiece 12 is effectively placed in a position for immediate use by anyone holding the cap member 54. Upon removing the cap member 54 from the storage container 50, the breathing gas apparatus 8 and flashlight 28 assemblies are removed from the storage container 50. Thus, once the storage container 50 is located and the cap member 54 removed, the user has the entire apparatus in hand and ready for use. This facilitates the use of the breathing apparatus 8 of the invention.

The entire apparatus is further of a dimension which allows for easy storage in vehicles or buildings. The storage container 50 is preferably a 2 inch×2 inch×10 inch rectangular container. The flashlight 28 and connector housing 38 when are connected together for storage are preferably of an overall length of approximately 7 inches. This allows for the storage container 50 to have ample room to store all of the apparatus therein. These dimensions allow for convenient and readily accessible storage in vehicles, such as in glove boxes or under seats, and in buildings, such as in desk drawers or on shelves. The overall dimensions of the apparatus are sufficiently small so as to not become an obstacle to the user when confronted with an emergency situation.

When a user is confronted with an emergency situation of the type previously described, the invention functions to provide both a source of breathing gas and light. However, the features of the invention can be used in a number of ways. When stored in the storage container 50, the breathing apparatus 8 and flashlight 28 are connected together. When the apparatus is needed, the cap member 54 is removed from the storage container 50. This places the mouthpiece 12 effectively into the user's hand which is holding the cap member 54. Further movement of the cap member 54 causes the entire apparatus to be withdrawn from the container 50 to be grasped by the user's other hand. This allows for the user to place the mouthpiece 12 in his mouth and hold the flashlight 28 and breathing gas supply container 10 in one hand. In this manner, the user has ready access to the controls for both the flashlight 28 and the breathing apparatus 8. Adjustments can be quickly made to either of these devices.

Additionally, the flashlight 28 can be separated from the breathing gas supply container for independent use. The container 10 and connector housing 38 may be placed in a pocket on the user's clothes after the breathing apparatus 8 has been adjusted for proper gas flow. Then, the flashlight 28 may be utilized separately without the constraint of the tubing 14 which connects the container 10 to mouthpiece 12.

The flashlight 28 also has a number of characteristics which make the device particularly suitable for use when submerged under water. First, the flashlight 28 is waterproof. Additionally, the flashlight 28 is configured so as to float vertically. When a vehicle is submerged, the top of the vehicle does not necessarily correspond to the direction of the surface. The flashlight 28 automatically points upward when allowed to float, serving to indicate the direction to the surface and illuminate any likely avenues of escape. This feature also serves to indicate to wouldbe rescuers on the surface the location of the occupant of the vehicle submerged by directing light upward.

Having thus described my invention, it can be seen that numerous alternative configurations can be envisioned without departing from the spirit of this invention.

I, therefore, claim:

1. A portable emergency breathing apparatus, comprising:
a breathing gas supply container disposed within a connector housing;
a mouthpiece communicating with said breathing gas supply container;
a valve disposed between said mouthpiece and said breathing gas supply container to control the flow of gas from said breathing gas supply container to said mouthpiece; and
a flashlight removably affixed to said connector housing in a manner so that said flashlight may be used while it is affixed to said connector housing or detached and used apart from said connector housing.

2. The invention of claim 1, wherein said mouthpiece communicates with said breathing gas supply container through a length of elastomeric tubing.

3. The invention of claim 1, wherein said connector housing includes an internal access opening for receiving said breathing gas supply container, and a portion of said flashlight being disposed within said connector housing through said opening.

4. The invention of claim 1, wherein said portable emergency breathing apparatus is received within a storage container, said storage container including a container body and a removal cap member, said cap member having a handle secured to the exterior surface thereof, said handle being luminescent so as to be visible under and light conditions.

5. The invention of claim 1, wherein said flashlight is waterproof.

6. The invention of claim 1, wherein said connector housing is metal.

7. The invention of claim 4, wherein said mouthpiece is permanently secured to said cap member in a useable orientation proximate the interior surface of said cap member so that said mouthpiece is secured proximate said handle of said cap member for rapid location of said mouthpiece for emergency use and removal of said cap member from said container body causes said apparatus to be withdrawn from said storage container for emergency use.

8. The invention of claim 4, wherein said container body is configured with openings to allow use of said flashlight while said flashlight is received within said storage container.

9. The invention of claim 5, wherein said flashlight is configured to float vertically in the water.

10. A portable emergency breathing apparatus and storage assembly comprising:
a breathing gas supply container;
a mouthpiece communicating with said breathing gas supply container;
a valve disposed between said mouthpiece and said breathing gas supply container to control the flow of gas from said breathing gas supply container to said mouthpiece; and
a storage container adapted to receive said portable emergency breathing apparatus, said storage container including a container body and a removable cap member, said cap member having a handle secured to the exterior surface thereof and said mouthpiece being permanently secured to said cap member in a useable orientation proximate the interior surface of said cap member so that said mouthpiece is secured proximate said handle of said cap member for rapid location of said mouthpiece for emergency use and removal of said cap member from said container body causes said apparatus to be withdrawn from said storage container for emergency use.

11. The invention of claim 10, wherein said handle is luminescent so as to be visible under any light conditions.

12. The invention of claim 10, wherein said mouthpiece communicates with said breathing gas supply container through a length of elastomeric tubing.

13. The invention of claim 10, wherein a flashlight is removably affixed to said breathing gas supply container.

14. The invention of claim 13, wherein said container body is configured with openings to allow use of said flashlight while said flashlight is received within said storage container.

15. The invention of claim 13, wherein said breathing gas supply container is disposed within a connector housing, said connector housing being adapted to removably engage said flashlight.

16. The invention of claim 15, wherein said connector housing includes an internal access opening for receiving said breathing gas supply container, and a portion of said flashlight being disposed within said connector housing through said opening.

17. The invention of claim 15, wherein said connector housing is metal.

18. The invention of claim 15, wherein said flashlight is waterproof.

19. A portable emergency breathing apparatus and storage assembly comprising:
a metal connector housing having an internal recess opening;
a breathing gas supply container disposed within said connector housing;
a mouthpiece communicating with said breathing gas supply container through a length of elastomeric tubing;
a valve disposed between said mouthpiece and said breathing gas supply container;
a waterproof flashlight removably affixed to said connector housing, a portion of said flashlight being disposed within said connector housing through said internal access opening; and
a storage container adapted to receive said portable emergency breathing apparatus, said storage container including a container body and cap member, said container body being configured with openings to allow use of said flashlight while said flashlight is received within said storage container, said cap member having a luminescent handle secured to an exterior surface thereof, said mouthpiece being permanently secured to said cap member in a useable orientation proximate the interior surface of said cap member so that said mouthpiece is secured proximate said handle of said cap member for rapid location of said mouthpiece for emergency use and removal of said cap member from said container causes said apparatus to be withdrawn from said storage container for emergency use.

* * * * *